United States Patent [19]

Grill et al.

[11] Patent Number: 5,693,863
[45] Date of Patent: Dec. 2, 1997

[54] METHOD FOR THE PRODUCTION OF E-1-[4'-(2-DIMETHYLAMINOETHOXY)-PHENYL]-1-(3-HYDROXYPHENYL)-2-PHENYL-1-BUTENE

[75] Inventors: Helmut Grill, Vaterstetten; Axel Woschina, Poing, both of Germany

[73] Assignee: Klinge Pharma GmbH, Germany

[21] Appl. No.: 669,350

[22] PCT Filed: Jan. 3, 1994

[86] PCT No.: PCT/EP94/00001

§ 371 Date: Sep. 23, 1996

§ 102(e) Date: Sep. 23, 1996

[87] PCT Pub. No.: WO95/18786

PCT Pub. Date: Jul. 13, 1995

[51] Int. Cl.$^6$ .................... C07C 213/08
[52] U.S. Cl. .............. 564/324; 564/394; 564/443
[58] Field of Search .............. 564/324, 394, 564/443

[56] References Cited

U.S. PATENT DOCUMENTS

| | | | |
|---|---|---|---|
| 4,839,155 | 6/1989 | McCague | 424/1.1 |
| 4,960,937 | 10/1990 | Woschina et al. | 564/324 |

FOREIGN PATENT DOCUMENTS

| | | | |
|---|---|---|---|
| 0 054 168 | 6/1982 | European Pat. Off. | C07C 93/06 |
| 0 313 799 | 5/1989 | European Pat. Off. | C07C 93/06 |

OTHER PUBLICATIONS

J. Med. Chem. 82 vol. 85 vol. 25 pp. 1056–1060 (1982).

*Primary Examiner*—Brian M. Burn
*Attorney, Agent, or Firm*—Sughrue, Mion, Zinn, Macpeak & Seas, PLLC

[57] ABSTRACT

The present invention relates to methods for the production of E-1-[4'-(2-dimethylaminoethoxy)-phenyl]-1-(3'-hydroxyphenyl)-2-phenyl-1-butene of formula (I) which comprises heating the compound of formula (II) in the presence of an organic solvent and HCl gas and cooling the reaction to obtain the compound of formula (IIIa), and then heating the isolated compound of formula (IIIa) in the presence of sulfuric acid or hydrochloric acid to obtain the compound according to formula (I).

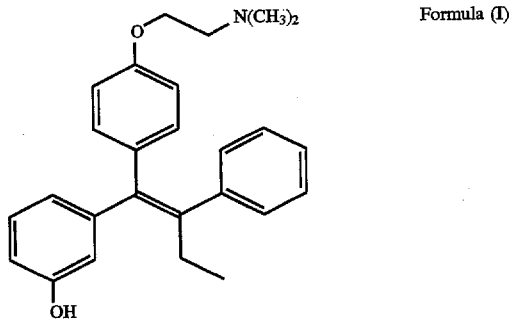

Formula (I)

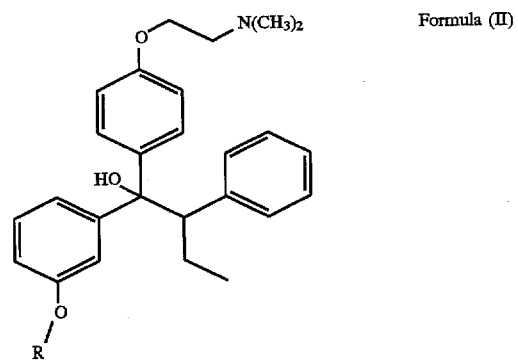

Formula (II)

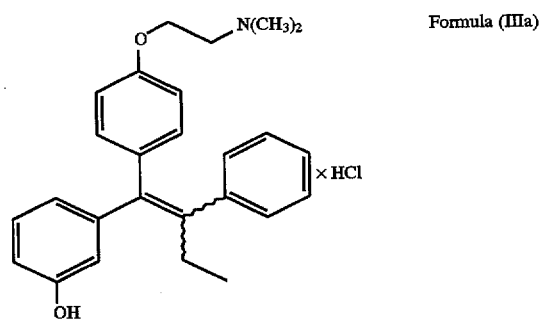

Formula (IIIa)

where R is an easily hydrolyzable protecting group

13 Claims, No Drawings

METHOD FOR THE PRODUCTION OF E-1-[4'-(2-DIMETHYLAMINOETHOXY)-PHENYL]-1-(3-HYDROXYPHENYL)-2-PHENYL-1-BUTENE

This application is a 35USC371 of PCT/EP94/00001, filed Jan. 3, 1994.

FIELD OF THE INVENTION

The present invention relates to novel methods for the production of E-1-[4'-(2-dimethylaminoethoxy)-phenyl]-1-(3'-hydroxyphenyl)-2-phenyl-1-butene (Droloxifene/INN) in exceptionally high yield and purity. This compound possesses valuable therapeutic properties in that it exhibits marked anti-estrogen effects and is useful in the treatment of hormone-dependent mammary tumors.

BACKGROUND ART

The compound having the formula (I)

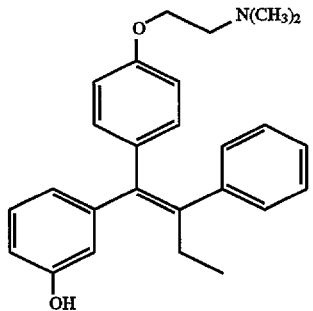

is disclosed in U.S. Pat. No. 5,047,431. A method for the production of E-1-[4'-(2-dimethylaminoethoxy)-phenyl]-1-(3'-hydroxyphenyl)-2-phenyl-1-butene is also described in U.S. Pat. No. 5,047,431 in which the E/Z-stereoisomer mixture of formula (III) as a free base

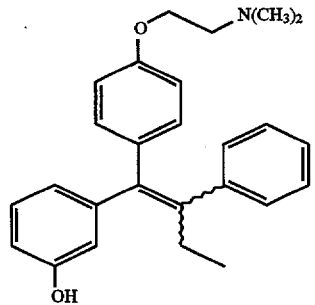

is obtained by dehydrating compounds of the general formula (II)

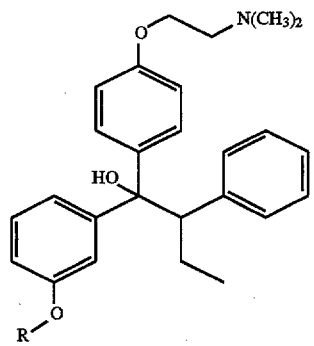

where R is an easily hydrolyzable protecting group in the presence of dilute hydrochloric acid. The yield of the E/Z-isomer mixture of formula (III) in this process is 90%. The E/Z-isomer mixture of formula (III) is subsequently isolated, refluxed in concentrated hydrochloric acid, and the hydrochloride of E-1-[4'-(2-dimethylaminoethoxy)-phenyl]-1-(3'-hydroxyphenyl)-2-phenyl-1-butene is isolated by crystallization with a yield of 48%. The E-isomer hydrochloride is then converted to E-1-[4'-(2-dimethylaminoethoxy)-phenyl]-1-(3'-hydroxyphenyl)-2-phenyl-1butene by crystallization (yield 96%). The entire process from compound (II) to compound (I) has a theoretical yield of 41% and involves a total of two synthetic and three crystallization steps. The afore-mentioned method is unsatisfactory due to the low yield of therapeutically active E-1-[4'-(2-dimethylaminoethoxy)-phenyl]-1-(3'-hydroxyphenyl)-2-phenyl-1-butene.

In EP 0313799, the process for the production of E-1-[4'-(2-dimethylaminoethoxy)-phenyl]-1-(3'-hydroxyphenyl)-2-phenyl-1-butene of formula (I) is disclosed in which the carbinol of formula (IV)

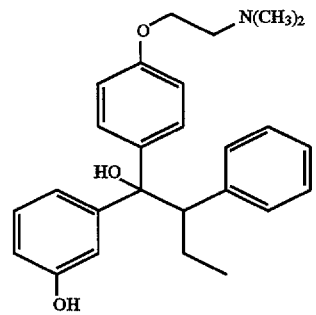

is reacted with either sulfuric acid or hydrochloric acid, and subsequently crystallized to give E-1-[4'-(2-dimethylaminoethoxy)-phenyl]-1-(3'-hydroxyphenyl)-2-phenyl-1-butene with yields ranging from 90–96% and purities ranging from 99.4–99.7%. The procedure disclosed in EP 0313799 has the disadvantages that the starting compound, the carbinol of formula (IV) is only obtained with a yield of 90% from the compound of formula (II) previously described in U.S. Pat. No. 5,047,431. Thus, the overall yield of the conversion of the compound of formula (II) to E-1-[4'-(2-dimethylaminoethoxy)-phenyl]-1-(3'-hydroxyphenyl)-2-phenyl-1-butene is only at best between 81 and 86%, and the total process involves two synthetic and three crystallization steps. Furthermore, the purity of E-1-[4'-(2-dimethylaminoethoxy)-phenyl]-1-(3'-hydroxyphenyl)-2-phenyl-1-butene obtained by the afore-mentioned methods is insufficient to allow for direct formulation of E-1-[4'-

(2- dimethylaminoethoxy)-phenyl]-1-(3'-hydroxyphenyl)-2-phenyl-1-butene into pharmaceutical preparations. Therefore, additional purification steps are necessary to obtain E-1-[4'-(2-dimethylaminoethoxy)-phenyl]-1-(3'-hydroxyphenyl)-2-phenyl-1-butene in a form sufficiently pure to use for the production of a medicinal preparation. The object of the present invention is to provide methods involving fewer steps than previously described methods for the production of E-1-[4'-(2-dimethylaminoethoxy) -phenyl] -1-(3'-hydroxyphenyl)-2-phenyl-1-butene from compounds of the general formula (II) which result in an excellent overall yield and exceptional purity of E-1-[4'-(2-dimethylaminoethoxy)-phenyl]-1-(3'-hydroxyphenyl)-2-phenyl-1-butene suitable for direct use in the formulation of pharmaceutical preparation.

BRIEF SUMMARY OF THE INVENTION

Surprisingly, it has been found that the carbinols of the general formula (II) can be directly converted to the E/Z-stereoisomer mixtures of formula (III) with remarkably high yield, and that the isolated E/Z-stereoisomer mixture can be converted to the biologically active E-1-[4'-(2-dimethylaminoethoxy)-phenyl]-1-(3'-hydroxyphenyl)-2-phenyl-1-butene with high yield and exceptional purity. The purity of the resulting products of the present invention allow for the direct formulation of pharmaceutical preparations, thereby circumventing the previous need to further purify E-1-[4'-(2-dimethylaminoethoxy)-phenyl]-1-(3'-hydroxyphenyl)-2-phenyl-1-butene for use in manufacturing pharmaceuticals.

DETAILED DESCRIPTION OF THE INVENTION

The present invention provides methods for the production of E-1-[4'-(2-dimethylaminoethoxy)-phenyl]-1-(3'-hydroxyphenyl) -2-phenyl-1-butene of formula I

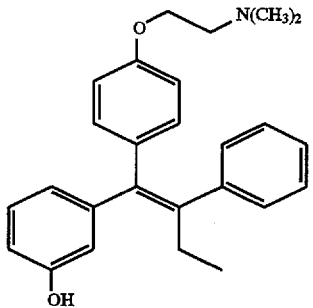

which comprises the steps of a) heating the compound of formula (II)

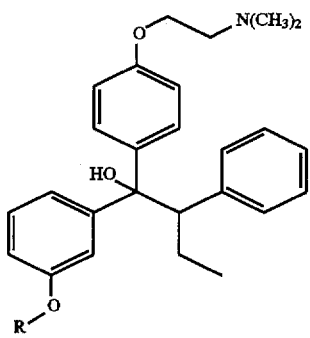

where R is an easily hydrolyzable protecting group, preferably a tetrahydropyranyl group, at a temperature within the range of 70°–80° C. for a time within the range of 4–6 hours in the presence of an organic solvent, preferably 2-propanol, and HCl gas, and then cooling the reaction to a temperature within a range of −5° to 5° C., preferably 0° C., for a time within the range of 4–6 hours, preferably 5.5 hours, to obtain E/Z-1-[4'-(2-dimethylaminoethoxy)-phenyl]-1-(3'-hydroxyphenyl)-2-phenyl-1-butene×hydrochloride of formula (IIIa)

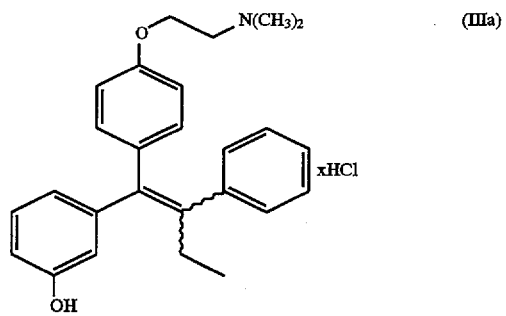

and b) heating the compound of formula(IIIa) at a temperature within the range of 50°–60° C. for a time within the range of 10–24 hours in the absence of an organic solvent and in the presence of 40–50% by volume sulfuric acid, preferably 50% by volume sulfuric acid, or 32–37% hydrochloric acid, preferably 37% hydrochloric acid. When sulfuric acid is used in step b, the E/Z-stereoisomer mixture of formula (IIIa) obtained by step a is heated at a temperature, preferably within the range of 55°–60° C. for a time of preferably 14 hours. When hydrochloric acid is used in step b, the E/Z-stereoisomer mixture of formula (IIIa) obtained by step a is heated at a temperature, preferably within the range of 50°–55° C. for a time of preferably 16 hours. When the ratio of the Z- to the E-stereoisomer of formula (IIIa) obtained by step a is greater than 3:7, and preferably greater than 5:1, the E/Z-stereoisomer mixture of formula (IIIa) is heated at a temperature preferably within the range of 55°–60° C. for a time of preferably 22–24 hours. Thereafter, the reaction mixture is alkalinized, preferably with a 25% solution of ammonia in an organic solvent, such as dichloromethane.

The following examples are set forth as representative and preferred embodiments of the present invention. These examples are not to be construed as limiting the scope of the invention in any manner. It should be understood that variations and modifications can be made while remaining within the spirit and scope of the invention.

EXAMPLE 1 a) 25 parts of 1-[4'-(2-dimethylaminoethoxy)-phenyl]-2-phenyl-1-[3'-(2-tetrahydropyranyloxy)-phenyl]-n-butan-1-ol in 150 parts 2-propanol are stirred and heated at a temperature of 70°–80° C. and hydrochloric gas is introduced. After ca. 5.5 hours, the suspension is cooled to 0° C. and kept at this temperature for 12 hours. The precipitate is filtered by vacuum and washed with 25 parts 2-propanol. After drying, 21 parts (96% theoretical yield) E/Z -1-(4'-2-dimethylaminoethoxy)-phenyl]-1-(3'-hydroxyphenyl)-2-phenyl-1-butene×HCl having a content of greater than 70% of the E-stereoisomer (1H-NMR) are obtained; melting point 215°–217° C.

1H-NMR-spectrum (CDCl$_3$/DMSO-d$_6$) (100 MHz, chemical shifts are given in ppm. TMS ($\delta$=0.0) s=singlet, t=triplet, q=quartet, m=multiplet):

0.9 (3H, t) CH$_2$CH$_3$ 2.4 (2H, q) CH$_2$CH$_3$ 2.88 s N(CH$_3$)$_2$/E-isomer, 2.95 s N(CH$_3$)$_2$/Z-isomer 3.4 (2H, t) CH$_2$N 4.3 t OCH$_2$/E-isomer, 4.5 t OCH$_2$/Z-isomer 6.2–7.1 (13H, m) aromatic protons 6.9 and 12.0 (wide) OH, NH$^+$.

b) 3 parts of E/Z-1-[4'-(2-dimethylaminoethoxy)-phenyl]-1-(3'-hydroxyphenyl)-2-phenyl-1-butene×HCl (isomer mixture) are stirred into 25 parts 37% hydrochloric acid and the suspension is heated at 50° C. for 16 hours with vigorous stirring. Subsequently the suspension is cooled and alkalinized by the addition of 15 parts ice and 50 parts dichloromethane with 25% ammonia. The organic phase is washed several times with water. After the removal of the organic solvent 2.6 parts (95% theoretical yield) of E-1-[4'-(2-dimethylaminoethoxy)-phenyl]-1-(3'-hydroxyphenyl)-2-phenyl-1-butene having a content of 100% of the E-stereoisomer (HPLC) remain. Crystals from acetone have a melting point of 164° C.

EXAMPLE 2 a) 25 parts of 1-[4'-(2-dimethylaminoethoxy)-phenyl]-2-phenyl-1-[3'-(2-tetrahydropyranyloxy)-phenyl]-n-butan-1-ol in 150 parts 2-propanol are stirred and heated at a temperature of 70°–80° C. and hydrochloric gas is introduced. After ca. 5.5 hours, the suspension is cooled to 0° C. and kept at this temperature for 12 hours. The precipitate is filtered by vacuum and washed with 25 parts 2-propanol. After drying, 21 parts (96% theoretical yield) E/Z -1-(4'-2-dimethylaminoethoxy)-phenyl]-1-(3'-hydroxyphenyl)-2-phenyl-1-butene×HCl having a content of greater than 70% of the E-stereoisomer (1H—NMR) are obtained; melting point 215°–217° C.

1H-NMR- spectrum (CDCl$_3$/DMSO-d$_6$) (100 MHz, chemical shifts are given in ppm. TMS ($\delta$=0.0) s=singlet, t=triplet, q=quartet, m=multiplet):

0.9 (3H, t) CH$_2$CH$_3$ 2.4 (2H, q) CH$_2$CH$_3$ 2.88 s N(CH$_3$)$_2$/E-isomer, 2.95 s N(CH$_3$)$_2$/Z-isomer 3.4 (2H, t) CH$_2$N 4.3 t OCH$_2$/E-isomer, 4.5 t OCH$_2$/Z-isomer 6.2–7.1 (13H, m) aromatic protons 6.9 and 12.0 (wide) OH, NH$^+$.

b) 6 parts of E/Z-1-[4'-(2-dimethylaminoethoxy)-phenyl]-1-(3'-hydroxyphenyl)-2-phenyl-1-butene×HCl (isomer mixture) are stirred into 33 parts 50% by volume sulfuric acid and heated at 55° C. for 14 hours with vigorous shaking. After the addition of 10 parts water and 80 parts toluene, the reaction mixture is alkalinized with 25% ammonia. After washing with water, the organic phase is concentrated by vacuum distillation and the resulting suspension is crystallized from toluene. The precipitate is filtered by vacuum and washed with 6 parts toluene. After drying, 5.3 parts (97% theoretical yield) of E-1-[4'-(2-dimethylaminoethoxy)-phenyl]-1-(3'-hydroxyphenyl)-2-phenyl-1-butene having a content of 100% of the E-stereoisomer (HPLC) remain. Crystals from acetic acid ethylester have a melting point of 164° C.

EXAMPLE 3

3 parts of E/Z-1-[4'-(2- dimethylaminoethoxy)-phenyl]-1-(3'-hydroxyphenyl)-2-phenyl-1-butene×HCl having a content of more than 90% of the Z-stereoisomer are stirred into 30 parts 50% by volume sulfuric acid and heated at a temperature of 55°–60° C. for 24 hours with vigorous shaking. Subsequently the reaction mixture is cooled and alkalinized by the addition of 8 parts water and 20 parts dichloromethane with 25% ammonia. The organic phase is washed with water. After the removal of the organic solvent by vacuum distillation, 2.3 parts (83% theoretical yield) of E-1-[4'-(2-dimethylaminoethoxy)-phenyl]-1-(3'-hydroxyphenyl)-2-phenyl-1-butene having a content of 99.8% of the E-stereoisomer (HPLC) remain. Crystals from ethanol have a melting point of 164° C.

EXAMPLE 4

A pharmaceutical preparation containing E-1-[4'-(2-dimethylaminoethoxy)-phenyl]-1-(3'-hydroxyphenyl)-2-phenyl-1-butene can be prepared by mixing 111 g, mannitol, 15 g, corn starch and 6 g, alginic acid, 20.0 g, and finely powdered E-1-[4'-(2-dimethylaminoethoxy)-phenyl]-1-(3'-hydroxyphenyl)-2-phenyl-1-butene, granulating the mixture and drying the granules. After carefully mixing the granules with 0.75 g, methyl cellulose and 1.5 g, magnesium stearate, the mixture is compressed into one thousand tablets, each containing 20 mg, active ingredient.

We claim:

1. A method for the production of E-1-[4'-(2-dimethylaminoethoxy)-phenyl]-1-(3 '-hydroxyphenyl)-2-phenyl-1-butene of formula (I)

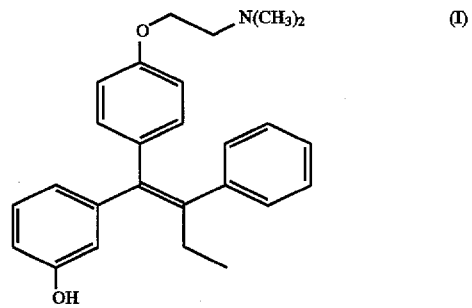

which comprises the steps of a) heating the compound of formula (II)

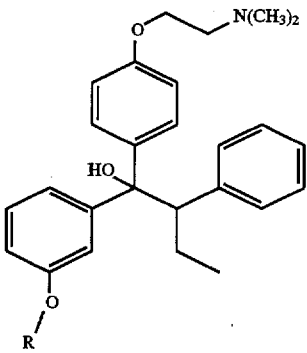
(II)

where R is an easily hydrolyzable protecting group at a temperature within the range of 70°–80° C. for a time within the range of 4–6 hours in the presence of an organic solvent and HCl gas and then cooling the reaction to a temperature within a range of –5° to 5° C. for a time within the range of 10–14 hours to obtain E/Z-1-[4'-(2-dimethylaminoethoxy)-phenyl]-1-(3'-hydroxyphenyl) -2-phenyl-1-butene×hydrochloride of formula (IIIa), and

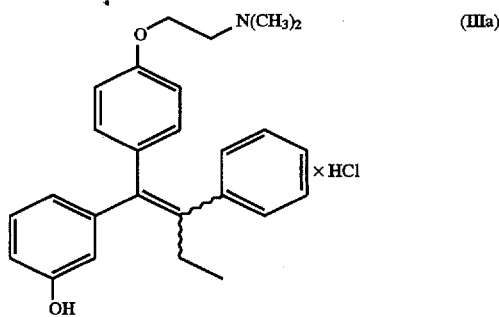
(IIIa)

b) heating the compound of formula(IIIa) at a temperature within the range of 50°–60° C. for a time within the range of 10–24hours in the absence of an organic solvent and in the presence of 40–50% by volume sulfuric acid or 32–37% hydrochloric acid, and alkalinizing the reaction mixture to obtain the compound according to formula (I).

2. A method according to claim 1 characterized in that the organic solvent of step a is 2-propanol.

3. A method according to claim 1 characterized in that the reaction mixture of step a is cooled at 0° C.

4. A method according to claim 1 characterized in that the reaction mixture of step a is cooled for 12 hours.

5. A method according to claim 1 characterized in that the protecting group of R of formula (II) is a tetrahydropyranyl group.

6. A method according to claim 1 characterized in that the reaction mixture of step b is heated for a time within the range of 14–16 hours.

7. A method according to claim 1 characterized in that sulfuric acid is present in the reaction mixture of step b at 48–50% volume.

8. A method according to claim 7 characterized in that the reaction mixture of step b is heated at a temperature within the range of 55°–60° C.

9. A method according to claim 7 characterized in that the reaction mixture of step b is heated for a time within the range of 22–24 hours.

10. A method according to claim 1 characterized in that hydrochloric acid is present in the reaction mixture of step b at 35–37%.

11. A method according to claim 10 characterized in that the reaction mixture of step b is heated at a temperature within the range of 50°–60°.

12. A method according to claim 10 characterized in that when the ratio of the Z- to the E-stereoisomer of the compound of formula (IIIa) produced in step a is greater than 3:7, the reaction mixture of step b is heated for a time within the range of 14–24 hours.

13. A method according to claim 10 characterized in that when the ratio of the Z- to the E-stereoisomer of the compound of formula (IIIa) produced in step a is greater than 5:1, the reaction mixture of step b is heated at a time within the range of 22–24 hours.

* * * * *